United States Patent [19]

Siegfried

[11] Patent Number: 5,676,934
[45] Date of Patent: *Oct. 14, 1997

[54] DRY SUNSCREEN COMPOSITION

[75] Inventor: Robert W. Siegfried, Medford, N.J.

[73] Assignee: International Creations, Ltd., Chicago, Ill.

[*] Notice: The term of this patent shall not extend beyond the expiration date of Pat. No. 5,445,815.

[21] Appl. No.: 477,692

[22] Filed: Jun. 7, 1995

Related U.S. Application Data

[63] Continuation-in-part of Ser. No. 155,600, Nov. 22, 1993, Pat. No. 5,445,815.

[51] Int. Cl.$^6$ .................................................. A61K 7/42
[52] U.S. Cl. ............................. 424/59; 424/60; 514/938
[58] Field of Search ....................... 424/59, 60; 514/938

[56] References Cited

U.S. PATENT DOCUMENTS

| | | |
|---|---|---|
| 3,966,902 | 6/1976 | Chromecek ................. 424/59 |
| 4,172,122 | 10/1979 | Tubik et al. ................. 424/59 |
| 4,522,807 | 6/1985 | Kaplan ..................... 424/59 |
| 4,690,825 | 9/1987 | Won ....................... 514/847 |
| 4,724,240 | 2/1988 | Arbutyn .................... 514/847 |
| 4,855,127 | 8/1989 | Abrutyn et al. .............. 424/59 |
| 4,880,617 | 11/1989 | Chromecek et al. ........... 424/59 |
| 5,208,038 | 5/1993 | Gressani et al. ............. 424/489 |
| 5,445,815 | 8/1995 | Siegfried .................. 424/59 |

FOREIGN PATENT DOCUMENTS

| | | |
|---|---|---|
| 2608533 | 9/1976 | Germany . |
| 63-243012 | 10/1988 | Japan . |

OTHER PUBLICATIONS

Doi, et al., "Microencapsulated ultraviolet light–absorbing agents for cosmetics", 89: 168971d, *Chemical Abstracts*, vol. 89, 1978.

Pola Chemical industries, Inc., "Cosmetic sunscreens containing resin powder", 97: 1505894, *Chemical Abstracts*, vol. 97, 1982.

Layton, D.G., "Preservation and protection of active substances", 99: 54778x *Chemical Abstracts*, vol. 99, 1983.

(List continued on next page.)

*Primary Examiner*—Shelley A. Dodson
*Attorney, Agent, or Firm*—Henderson & Strum

[57] ABSTRACT

A dry sunscreen composition comprising effective amounts of octyl methoxycinnamate, octyl salicylate, homosalate, menthyl anthranilate, octocrylene, benzohenone-3, propylparaben, BHT, PVP/eicosene copolymer, octyldodecyl neopentanoate, $C_{12-15}$ alcohols benzoate, titanium dioxide, and acrylates copolymer. A process for preparing a dry sunscreen composition that involves: combining effective amounts of octyl methoxycinnamate, octyl salicylate, homosalate, menthyl anthranilate, octocrylene, benzohenone-3, propylparaben, BHT, and PVP/eicosene copolymer to form a first section of ingredients; heating the first section of ingredients to a sufficient temperature with substantially constant mixing until it becomes clear and homogenous; combining effective amounts of $C_{12-15}$ alcohols benzoate, and octyldodecyl neopentanoate to form a second section of ingredients by mixing at substantially ambient temperature; adding effective amounts of titanium dioxide and coloring agent to the second section of ingredients by mixing at ambient temperature until it becomes a uniform paste; adding the uniform paste to the first section of ingredients to form a homogenous fluid; milling the homogenous fluid at a sufficient temperature until a predetermined size is obtained; heating the milled homogenous fluid to a predetermined temperature; adding a first amount of acrylates copolymer to the milled homogenous fluid and mixing to form a third section of ingredients; and adding the third section of ingredients to additional acrylates copolymer and mixing until it forms a homogenous dry sunscreen composition.

24 Claims, 1 Drawing Sheet

Coefficient of Absorbance Comparison
Dry Sunscreen and Westwood 29

Wavelength in Nanometers

I Dry Sunscreen    + Westwood 29

OTHER PUBLICATIONS

Vanlerbergne, et al, "Composition containing aqueous dispersions of lipid Spherules", 91: 96523, *Chemical Abstracts*, vol. 91, 1978.

Chromecek, et al, "Solid diffusion system for emitting a composition for improving the odor of the air", 85: 178439t, *Chemical Abstracts*, vol. 85, 1976.

Yamaguchi, et al, "Cosmetic materials containing porous polymer gels", 110: 218827m, *Chemical Abstracts*, vol. 110, 1989.

Article entitled "Industrial News", *Happi*, Jan. 1992.

Article entitled "Laboratory and Human Exposure Evaluation of Unique Sunscreen Formulations", J. Soc. Cosmet. Chem., 24, 541–550, Aug. 19, 1973.

Charles Fox, "Sunscreen and Suntan Products: Patent and Literature Update", *Cosmetics & Toiletries*, vol. 102, Mar. 1987.

Robert Y. Lochhead, "Encyclopedia of Polymers and Thickeners for Cosmetics", *Cosmetics & Toiletries*, vol. 103, Dec. 1988.

Fig. 1

DRY SUNSCREEN COMPOSITION

RELATED APPLICATION

This application is a Continuation-In-Part application of Ser. No. 08/155,600, filed Nov. 22, 1993 and now U.S. Pat. No. 5,445,815, the disclosure of which in its entirety is incorporated by reference thereto herein.

BACKGROUND ART

Conventional sunscreen products are lotions employing a carrier generally consisting of a water-based emulsion which serves primarily as an aid in dispersing the active ingredients on the skin. As the carrier water, evaporates from conventional products, a thin film of active ingredient plus excipient is deposited on the skin. The film left behind on the skin is then the portion of the product which lends protection from ultraviolet radiation. High temperature extremes can cause the emulsion to separate leading to unusable product and often leakage. At low temperature extremes, such as those present in a snow skiing environment, the product may freeze and be unusable. Also, high SpF rated emulsion products typically have a greasy feel and makes it difficult for the user to grip tools or sporting equipment.

Those concerned with these and other problems recognize the need for an improved sunscreen composition.

DISCLOSURE OF THE INVENTION

An object of the present invention is the provision of an improved sunscreen composition.

Another object is to provide a sunscreen composition that is applied as a dry powder.

A further object of the invention is the provision of a sunscreen composition that is not sensitive to high or low temperature extremes.

Still another object is to provide a sunscreen composition having a high concentration of active ingredients.

A still further object of the present invention is the provision of a sunscreen composition that is non-greasy, safe and convenient to use.

The present invention is directed to dry sunscreen compositions, including a highly crosslinked polymethacrylate copolymer powder combined with sunscreen ingredients.

The present invention is also directed to processes for preparing dry sunscreen compositions comprising the steps of combining effective amounts of sunscreen ingredients with a highly crosslinked polymethacrylate copolymer powder in the manner discussed in more detail herein.

BRIEF DESCRIPTION OF THE DRAWINGS

These and other attributes of the invention will become more clear upon a thorough study of the following description of the present invention including the best mode for carrying out the invention, particularly when reviewed in conjunction with the examples and the drawings wherein:

The FIGURE (FIG. 1) is a graph illustrating the comparison of coefficients of absorbance for the dry sunscreen of the present invention and a commercially available product.

DETAILED DESCRIPTION

In general, dry sunscreen compositions in accordance with the present invention comprise effective amounts of active sunscreen ingredients in sufficient amounts effective to result in a dry sunscreen composition capable of providing a desired degree of sunscreen protection.

More specifically, the dry sunscreen compositions of the present invention comprises ingredients selected from a group of ingredients comprising:

sunscreen active ingredients selected from the group consisting of: octyldimethyl paba, octyl methoxycinnamate, octyl salicylate; homosalate, menthyl anthranilate, octocrylene, benzohenone-3, titanium oxide, and zinc oxide;

biocides selected from the group consisting of butylparaben and propylparaben;

antioxidants selected from the group consisting of BHA, tocopherol, and BHT;

substantivity aids selected from the group consisting of tricontanyl PVP and PVP/eicosene copolymer;

emollients, such as octyldodecyl neopentanoate; emollients and solvents selected from the group consisting of: esters of propylene glycol, isopropyl alcohol, glycerine, and isobutyl alcohol; octanol esters of $C_6$–$C_{18}$ fatty acids; and $C_{12\text{-}15}$ alcohols benzoate, also referred to as $C_{12}$–$C_{15}$ alkyl benzoate;

coloring agents selected from the group consisting of D&C lakes, FD&C color lakes, and iron oxides; and entrapment polymers, such as acrylates copolymers wherein said copolymer has a formula with the following general structure:

$$\left[\begin{array}{c} CH_3 \\ | \\ -CH_2-CH- \\ | \\ C=O \\ | \\ O \\ | \\ R \\ | \\ O \\ | \\ C=O \\ | \\ CH_2-C- \\ | \\ CH_3 \end{array}\right]_x \left[\begin{array}{c} CH_3 \\ | \\ C-CH_2- \\ | \\ C=O \\ | \\ O \\ | \\ R \end{array}\right]_y$$

For purposes of the present invention R comprises an alkyl group, and x and y are repeating units. Preferably, R is selected from at least one member of a group consisting of ethyl groups and dodecyl groups. For purposes of the present invention, the most preferred ethyl group has a formula: —$CH_2CH_2$—; and the most preferred dodecyl group has a formula: —$(CH_2)_{11}CH_3$. The ratio of x to y may be within the range of about 100:20 to about 60:20 and is most preferably about 80:20.

Most preferably, for purposes of the present invention, the acrylates has the following formula:

$$\left[\begin{array}{c} CH_3 \\ | \\ -CH_2-CH- \\ | \\ C=O \\ | \\ O \\ | \\ R' \\ | \\ O \\ | \\ C=O \\ | \\ CH_2-C- \\ | \\ CH_3 \end{array}\right]_x \left[\begin{array}{c} CH_3 \\ | \\ C-CH_2- \\ | \\ C=O \\ | \\ O \\ | \\ R'' \end{array}\right]_y$$

wherein R' is —$CH_2CH_2$— and R'' is —$(CH_2)_{11}CH_3$, and the ratio of x to y is about 80:20.

In general, the process for preparing dry sunscreen compositions in accordance with the present invention, comprise the steps of:

combining effective amounts of:

at least one sunscreen active ingredient selected from the group consisting of octyldimethyl paba, octyl methoxycinnamate, octyl salicylate, homosalate, menthyl anthranilate; octocrylene; and benzohenone-3;

at least one biocide selected from the group consisting of butylparaben and propylparaben;

at least one antioxidant selected from the group consisting of BHA, tocopherol, and BHT; and at least one substantivity aid selected from the group consisting of tricontanyl PVP and PVP/eicosene copolymer to form a first section of ingredients;

heating the first section of ingredients to a sufficient temperature preferably within the range of about 70° C. to about 85° C. and more preferably within the range of about 75° C. to about 80° C., with substantially constant mixing until it becomes clear and homogenous;

combining effective amounts of:

at least one emollient and solvent selected from the group consisting of esters of propylene glycol, isopropyl alcohol, glycerine, isobutyl alcohol; octanol esters of $C_6$–$C_{18}$ fatty acids; and $C_{12-15}$ alcohols benzoate; and octyldodecyl neopentanoate;

to form a second section of ingredients by mixing at substantially ambient temperature;

adding effective amounts of:

at least one sunscreen active ingredient selected from the group consisting of zinc oxide and titanium dioxide; and, optionally, at least one coloring agent selected from the group consisting of D&C lakes, FD&C color lakes, and iron oxides, to the second section of ingredients by mixing at ambient temperature until it becomes a uniform paste;

adding the uniform paste to the first section of ingredients to form a homogenous fluid;

milling the homogenous fluid at a sufficient temperature, preferably within the range of about 60° C. to about 85° C. and more preferably within the range of about 70° C. to about 80° C., until a predetermined size is obtained;

heating the milled homogenous fluid to a predetermined temperature;

adding a first amount of acrylates copolymer to the milled homogenous fluid and mixing to form a third section of ingredients; and adding the third section of ingredients to additional acrylates copolymer and mixing until it forms a homogenous dry sunscreen composition, preferably wherein said acrylates copolymer has a formula and structure, as described herein.

Preferably the process for preparing sunscreen compositions in accordance with the present invention, as described herein, includes the step of holding the homogenous dry sunscreen composition in a sealed container for about twenty-four hours, whereby complete absorbance of the milled homogenous fluid onto the acrylates copolymer is achieved.

In accordance with the present invention, it is critical that the sunscreen compositions of the present invention comprise at least one ingredient selected from the group consisting of the following sunscreen active ingredients:

octyldimethyl paba, octyl methoxycinnamate, octyl salicylate; homosalate, menthyl anthranilate, octocrylene, benzohenone-3, titanium oxide, and zinc oxide;

For purposes of the dry sunscreen composition of the present invention and the process for its preparation, ingredients may be combined during processing, as described above, in amounts so as to result in a dry sunscreen composition comprising ingredients that are present in the dry sunscreen composition in effective amounts as follows:

at least one ingredient selected from the group consisting of:

an ingredient selected from the group consisting of octyldimethyl paba and octyl methoxycinnamate which may be present in amounts up to about 8.0 wt %, and preferably up to about 7.5 wt %; and preferably which are present in an amount within the range of 1.4 wt % to about 8.0 wt % for octyldimethyl paba, and an amount within the range of about 2.0 wt % and about 7.5 wt % for octyl methoxycinnamate;

octyl salicylate which may be present in an amount up to about 5 wt %, and preferably is present in an amount within the range of about 3.0 wt % to about 5.0 wt %;

homosalate which may be present in amounts up to about 15 wt %, and preferably is present in an amount within the range of about 4.0 wt % to about 15.0wt %;

menthyl anthranilate which may be present in amounts up to about 5 wt %, and preferably is present in an amount within the range of about 3.5 wt % to about 5.0 wt %;

octocrylene which may be present in amounts up to about 10 wt %, and preferably is present in an amount within the range of about 7.0 wt % to about 10.0 wt %;

benzohenone-3 (oxybenzone) which may be present in an amount up to about 6 wt %, and preferably is present in amounts within the range of about 2.0 wt % to about 6.0 wt %; and an ingredient selected from the group consisting of titanium dioxide and zinc oxide which may be present in amounts up to about 25 wt %, and preferably is present in an amount within the range of about 2.00 wt % to about 25.00 wt %.

In addition to at least one of the above-listed sunscreen active ingredients, the sunscreen compositions of the present invention also comprise:

biocides selected from the group consisting of butylparaben and propylparaben present in amounts within the range of about 0.01 wt % to about 0.2 wt %;

antioxidants selected from the group consisting of BHA, tocopherol and BHT present in amounts within the range of about 0.01 wt % to about 0.2 wt %;

substantivity aids selected from the group consisting of tricontanyl PVP and PVP/eicosene copolymer present in amounts within the range of about 0.25 wt % to about 10.0 wt %.

emollients, such as octyldodecyl neopentanoate, present in amounts within the range of about 0.5 wt % to about 10.0 wt %; and solvents selected from the group consisting of $C_{8-12}$ alkyl esters of: propylene glycol, isopropyl alcohol, glycerine, isobutyl alcohol; octanol esters of $C_6$–$C_{18}$ fatty acids; and $C_{12-15}$ alcohols benzoate present in amounts within the range of about 0.5 wt % to about 10.0 wt %; and entrapment polymers selected from the group consisting of acrylates copolymers present in amounts within the range of about 10 wt % to about 40 wt %.

Optionally, coloring agents selected from the group consisting of D&C lakes, FD&C color lakes and iron oxides may be present in amounts up to about 0.3 wt %; and are preferably present in amounts within the range of about 0.01 wt % to about 0.30 wt %.

For purposes of the dry sunscreen composition of the present invention and the process for its preparation, the ingredients are more preferably combined during processing, as described above, in amounts so as to result in a dry sunscreen composition comprising ingredients that are present in the dry sunscreen composition in effective amounts as follows:

sunscreen active ingredients selected from the group consisting of:

octyldimethyl paba present within the range of 1.4 wt % to about 8.0 wt % or octyl methoxycinnamate present in amounts within the range of about 2.0 wt % and about 7.5 wt %;

octyl salicylate present in an amount within the range of about 3.0 wt % to about 5.0 wt %;

homosalate present in an amount within the range of about 4.0 wt % to about 15.0 wt %;

menthyl anthranilate present in an amount within the range of about 3.5 wt % to about 5.0 wt %;

octocrylene present in an amount within the range of about 7.0 wt % to about 10.0 wt %;

benzohenone-3 (oxybenzone) present in an amount within the range of about 2.0 wt % to about 6.0 wt %; and zinc oxide or titanium dioxide present in an amount within a range of about 2.0 wt % to about 25 wt %.

In addition to the above-identified list of sunscreen active ingredients, the dry sunscreen compositions in accordance with this more preferred embodiment of the present invention also comprise:

biocides selected from the group consisting of butylparaben and propylparaben present in amounts within the range of about 0.01 wt % to about 0.2 wt %;

antioxidants selected from the group consisting of BHA or tocopherol and BHT present in amounts within the range of about 0.01 wt % to about 0.2 wt %;

substantivity aids selected from the group consisting of tricontanyl PVP and PVP/eicosene copolymer present in amounts within the range of about 0.25 wt % to about 10.0 wt %;

emollients, such as octyldodecyl neopentanoate present in amounts within the range of about 0.5 wt % to about 10.0 wt %; and solvents selected from the group consisting of $C_{8-12}$ alkyl esters of: propylene glycol, isopropyl alcohol, glycerine, isobutyl alcohol; and octanol esters of $C_6$–$C_{18}$ fatty acids and $C_{12-15}$ alcohols benzoate, also referred to as $C_{12}$–$C_{15}$ alkyl benzoate, present in amounts within the range of about 0.5 wt % to about 10.0 wt %;

entrapment polymers selected from the group consisting of acrylates copolymers present in amounts within the range of about 10 wt % to about 40 wt %; and, optionally, coloring agents selected from the group consisting of D&C lakes, FD&C color lakes and iron oxides present in amounts up to about 0.3 wt %; and are present preferably in amounts within the range of about 0.01 wt % to about 0.30wt %.

In the most preferred embodiment of the present invention, the dry sunscreen composition of the present invention comprise ingredients and amounts of ingredients as follows:

octyl methoxycinnamate present in an amount within the range of about 2 wt % to about 7.5 wt %; octyl salicylate present in an amount within the range of about 3 wt % to about 5 wt %; homosalate present in an amount within the range of about 4 wt % to about 15 wt %; menthyl anthranilate present in an amount within the range of about 3.5 wt % to about 5 wt %; octocrylene present in an amount within the range of about 7 wt % to about 10 wt %; benzohenone-3 (oxybenzone) present in an amount within the range of about 2 wt % to about 6 wt %; titanium dioxide present in an amount within the range of about 2 wt % to about 25 wt %; propylparaben present in an amount within the range of about 0.01 wt % to about 2.0 wt %; BHT present in an amount within the range of about 0.01 wt % to about 2.0 wt %; PVP/eicosene copolymer present in an amount within the range of about 0.25 wt % to about 10.0 wt %; octyldodecyl neopentanoate present in an amount within the range of about 0.5 wt % to about 10.0 wt %; $C_{12-15}$ alcohols benzoate are present in amounts within the range of about 0.5 wt % to about lo.0 wt %; and polymethacrylate copolymer, as the acrylates copolymer, present in an amount within the range of about 10.0 wt % to about 40.0 wt %.

The most preferred composition for the dry sunscreen composition of the present invention comprises about 7.50 weight percent octyl methoxycinnamate, about 5.00 weight percent octyl salicylate, about 15.00 weight percent homosalate, about 5.00 weight percent menthyl anthranilate, about 10.00 weight percent octocrylene, about 6.00 weight percent benzohenone-3, about 0.05 weight percent propylparaben, about 0.05 weight percent BHT, about 4.49 weight percent PVP/eicosene copolymer, about 5.75 weight percent octyldodecyl neopentanoate, about 5.75 Weight percent C12–15 alcohols benzoate, about 10.00 weight percent titanium dioxide, about 0.15 weight percent coloring agent, and about 25.26 weight percent polymethacrylate copolymer.

BEST MODE FOR CARRYING OUT THE INVENTION

The following examples are illustrative of the best mode for carrying out the invention. They are obviously not to be construed as limitative of the invention since various other embodiments can readily be evolved in view of the teachings provided herein.

EXAMPLE 1

The dry sunscreen of the present invention is a significant departure from current conventional sunscreen products in that it uses a highly crosslinked polymethacrylate copolymer powder as the application vehicle.

Table 1 provides a positive identification of each of the ingredients used in the dry sunscreen formulation of the present invention. The identification includes the Cosmetic, Toiletry and Fragrance Association (CTFA) name and the Chemical Abstracts Number (CAS#).

TABLE 1

DRY SUNSCREEN INGREDIENTS

| Trade Name/ Supplier | CTFA Name | Description | CAS # |
|---|---|---|---|
| N/A | Octyl Methoxycinnamate | 3-(4-Methoxyphenol)-2-Propenoic Acid, 2-Ethylhexyl Ester | 5466-77-3 |
| N/A | Octyl Salicylate | Benzoic Acid, 2-Hydroxy-,2-Ethylhexyl Ester | 118-60-5 |
| N/A | Menthyl Anthranilate | Cyclohexanol, 5-Methyl-2-(1-Methylethyl),-2 Aminobenzoate | 134-09-8 |
| N/A | Homosalate | Benzoic Acid, 2-Hydroxyl-3,3,5-Thrimethylcyclohexyl Ester | 118-56-9 |
| N/A | Octocrylene | 2-Ethylhexyl 2 Cyano-3,3-Diphenylacrylate | 6197-30-4 |
| N/A | Benzohenone-3 | 2-Hydroxy-4-Methoxybenzophenone | 131-57-7 |

TABLE 1-continued

DRY SUNSCREEN INGREDIENTS

| Trade Name/ Supplier | CTFA Name | Description | CAS # |
|---|---|---|---|
| N/A | Propylparaben | 4-Hydroxybenzoic Acid, Propyl Ester | 94-13-3 |
| N/A | BHT | 2,6-Bis(1,1-Dimethylethyl)-4-Methylphenol | 128-37-0 |
| Ganex V220 (ISP) | PVP/Eicosene Copolymer | 1-Eicosene, Polymer with 1 Ethenyl-2-Pyrrolidinone | 28211-18-9 |
| Finsolv TN (Finetex Chemicals) | C12–15 Alcohols Benzoate (Patented Material) | Linear Primary Alcohols Benzoate Ester | |
| Elfac 1-205 (Alzo Inc.) | Octyldodecyl Neopentanoate (Patent 5,116,604) | | 125496-22-2 |
| Micronized Trtanium Dioxide SA-20 (Grant Industries) | Titanium Dioxide | Titanium Dioxide | 13463-67-7 |
| N/A | D&C Yellow No. 5 Aluminum Lake | The aluminum salt of FD & C Yellow No. 5 extended on an appropriate substrate in compliance with 21 CFR 82.1051 | 977058-75-5 |
| Polytap Q5-6603 (Dow Corning) | Acrylates Copolymer (Patented material) | | 977069-05-8 |

Table 2 provides a grouping of ingredients into sections and the weight of each ingredient. It is to be understood that the typical variation will be at least 0.01% for each ingredient.

TABLE 2

DRY SUNSCREEN FORMULA

| Section | Ingredient | % W/W | 1000 gms |
|---|---|---|---|
| A | Octyl Methoxycinnamate | 7.50 | 75 gm |
| | Octyl Salicylate | 5.00 | 50 gm |
| | Homosalate | 15.00 | 150 gm |
| | Menthyl Anthranilate | 5.00 | 50 gm |
| | Octocrylene | 10.00 | 100 gm |
| | Benzohenone-3 | 6.00 | 60 gm |
| | Propylparabon | 0.05 | 0.5 gm |
| | BHT | 0.05 | 0.5 gm |
| | Ganex V220 | 4.49 | 44.9 gm |
| B | Finsolu TN | 5.75 | 57.5 gm |
| | Elfac 1-205 | 5.75 | 57.5 gm |
| C | Micronized Titanium Dioxide SA-20 | 10.00 | 100 gm |
| | D & C Yellow No. 5 Aluminum Lake | 0.15 | 1.50 gm |
| D | Polytrap QS-6603 | 7.70 | 77.00 gm |
| E | Polytrap 05-6603 | 17.56 | 175.60 gm |

The ingredients are formulated to the finished dry sunscreen composition by the following process steps. Reference to Section A, Section B, etc. relate to the groups of ingredients in Table 2.

1. Combine ingredients in section A. Heat to 75° C.+/−5° C. with constant mixing using a propeller mixer. Mix until clear and homogeneous. Maintain at 75° C.+/−5° C. with continuous slow mixing.

2. Combine Section B ingredients. Mix with spatula at ambient temperature.

3. Add Section C ingredients to Section B at ambient temperature. Mix with a spatula to obtain a uniform paste.

4. Add Section CB to section A. Mix until homogeneous fluid is obtained.

5. Pass Section ABC through a 3-roller mill at 75° C.+/−5° C. Remill until a #7 grind on a Hegman gauge is obtained.

6. Return section ABC to hot bath and reheat to 75° C.+/−5° C.

7. Add Section D ingredient to Section ABC. Mix with a propeller mixer while scraping product off the side of the beaker with a spatula.

8. Weight Section E ingredient into a 3000 ml beaker.

9. Remove Section ABCD from heat and gradually add it to Section E continually mixing with a wide spatula.

10. When mixture seems homogeneous stop mixing. Seal beaker with plastic and hold for 24 hours so that absorbance of fluid into resin can be completed.

In an embodiment wherein titanium dioxide, zinc oxide and coloring agents are not included in the sunscreen formulation, step 3, as described above, may be omitted and the process proceeds directly from step 2 to step 4.

The advantages offered by the dry sunscreen are significant. Dry sunscreen can be stored indefinitely and at temperature extremes. The esthetics and functionality are not diminished by high or low temperature extremes. This aspect of the dry sunscreen is particularly applicable to the outdoor sports market. Golfers for example, often keep sunscreen products in their golf bag. During storage in automobile trunks and during golfing, the golf bag and sunscreen contained in it are exposed to high temperature extremes. High temperature extremes can, in the case of conventional sunscreen products, cause the emulsion to separate, leading to a non-usable product and often leakage of the product contents onto equipment being kept in the golf bag. These problems do not occur with the dry sunscreen. At low temperature extremes the benefits of the dry sunscreen are that, unlike most water-based emulsions, it does not freeze and is usable. Low temperature usability has particular application for snow skiers. In addition to low temperature usability, due to the fact that the dry sunscreen utilizes a powder carrier system, the product will not spill onto ski clothing and equipment as conventional products can. Dry sunscreen, due to the polymer entrapment system used as a delivery vehicle, produces a very dry and non-greasy film on skin. This non-greasy property is important particularly for usage during outdoor sports, and outdoor work applications. The non-greasy characteristic enables users to better maintain their grip on tools and athletic equipment. Dry sunscreen is extremely waterproof due both to its unique carrier system and the composition of the entrapped fluid. Being extremely waterproof, dry sunscreen has particular application for outdoor sports and outdoor work applications. Dry sunscreen is 2 to 2.5 times as concentrated as conventional sunscreen products. The dry copolymer powder carrier system permits high levels of sunscreen active ingredient loading, resulting in a product that requires a lower mg/cc dosage to achieve high SpF. The concentrated nature of the dry sunscreen then results in a light weight product that ships more easily and can be easily stored.

EXAMPLE 2

In clinical SpF evaluations (21 CFR 352.43), the sunscreen test sample is uniformly spread over a 50 $cm^2$ area of the human back. The amount of test sample utilized is sufficient to dose the area at 2 $mg/cm^2$ (or 0.1 gm to the 50 $cm^2$ area). Since the dry sunscreen does not contain a conventional carrier system (water-based emulsion) which evaporates prior to the formation of protective film, it is more concentrated in respect to the sunscreen active ingredients than the type of formula being considered by the test protocol described, as such, a much lower dosage of product would be required. Based on laboratory trials directed at determining the average amount of dry sunscreen that a consumer would apply to a given area of the skin, it was determined that a dry sunscreen dosage of 0.80–1.00 $mg/cm^2$ would be a reasonable application that would be expected to occur during actual usage (i.e. a 2.5 x concentration of active ingredients).

At 0.80–1.00 $mg/cm^2$, the dosage of sunscreen active ingredients remaining on the skin is roughly equivalent to the concentrations of sunscreen actives which would be deposited and remain on the skin following volitization of the water base using a conventional, water-based sunscreen lotion of SpF-29 dosed at 2 $mg/cm^2$. Active ingredient concentrations can be adjusted to achieve lower SpF values. Correlation of sunscreen active concentration to SpF was based on the attached "Sunscreen Evaluation" results shown in Table 3.

TABLE 3

SUNSCREEN EVALUATION

| Wavelength in NM. | Absorbence Dry Sunscreen | Coefficient ABS Dry Sunscreen | Coefficient ABS Westwood 29 |
| --- | --- | --- | --- |
| 215 | | 0 | 0 |
| 220 | | 0 | 0 |
| 225 | 0.0365 | 0.165522 | 0 |
| 230 | 0.3380 | 0.054235 | 0 |
| 235 | 0.3180 | 0.057285 | 0 |
| 240 | 0.2770 | 0.064186 | 0 |
| 245 | 0.1970 | 0.081227 | 0 |
| 250 | 0.1340 | 0.100495 | 0 |
| 255 | 0.1100 | 0.110363 | 0 |
| 260 | 0.1020 | 0.114139 | 0.120955 |
| 265 | 0.1160 | 0.107708 | 0.111281 |
| 270 | 0.1420 | 0.097596 | 0.098664 |
| 275 | 0.1790 | 0.086018 | 0.084913 |
| 280 | 0.2210 | 0.075479 | 0.073266 |
| 285 | 0.2540 | 0.068521 | 0.066212 |
| 290 | 0.2780 | 0.064006 | 0.062939 |
| 295 | 0.2930 | 0.061379 | 0.062413 |
| 300 | 0.3020 | 0.059866 | 0.062763 |
| 305 | 0.3090 | 0.058720 | 0.062588 |
| 310 | 0.3080 | 0.058882 | 0.062763 |

TABLE 3-continued

SUNSCREEN EVALUATION

| Wavelength in NM. | Absorbence Dry Sunscreen | Coefficient ABS Dry Sunscreen | Coefficient ABS Westwood 29 |
| --- | --- | --- | --- |
| 315 | 0.2870 | 0.062413 | 0.065838 |
| 320 | 0.2500 | 0.069314 | 0.072196 |
| 325 | 0.1990 | 0.080722 | 0.083036 |
| 330 | 0.1510 | 0.094523 | 0.096897 |
| 335 | 0.1150 | 0.108141 | 0.111746 |
| 340 | 0.0900 | 0.120397 | 0.125065 |
| 345 | 0.0660 | 0.135905 | 0.140670 |
| 350 | 0.0510 | 0.148796 | 0 |
| 355 | | 0 | 0 |
| 360 | | 0 | 0 |
| 365 | | 0 | 0 |
| 370 | | 0 | 0 |
| 375 | | 0 | 0 |
| 380 | | 0 | 0 |
| 385 | | 0 | 0 |
| 390 | | 0 | 0 |

Coefficient of correlation between the coefficients of absorbance of Dry Sunscreen and Westwood SPF29 = 0.996007

The evaluation of Table 3 compares the coefficient of absorbance as derived from scanning diluted samples of dry sunscreen and Westwood's SpF 29 lotion in a UV visible spectrophotometer at 260–345 nanometers. The gm/ml of the dry sunscreen fluid used in the test was reduced by a factor of 2.5 to account for the concentrated nature of the dry sunscreen and the lower dosage requirement.

The coefficient of absorbance is a measure of absorbance which factors into the calculation of the concentration of product in the sample dilution. The coefficient of absorbance calculation is derived from Beers Law and is as follows:

Coefficient of Absorbance=Natural Log (1/Absorbance) (concentrate in gm/ml)

The lower the number generated through the coefficient of absorbance calculation, the greater the blockage of the sample at that wavelength.

The solvent used in preparing diluted samples of test materials was anhydrous methanol. Use of anhydrous methanol as a solvent system causes a slight spectral shift of the data. This shift, however, is a common denominator to all samples.

Figure 1:
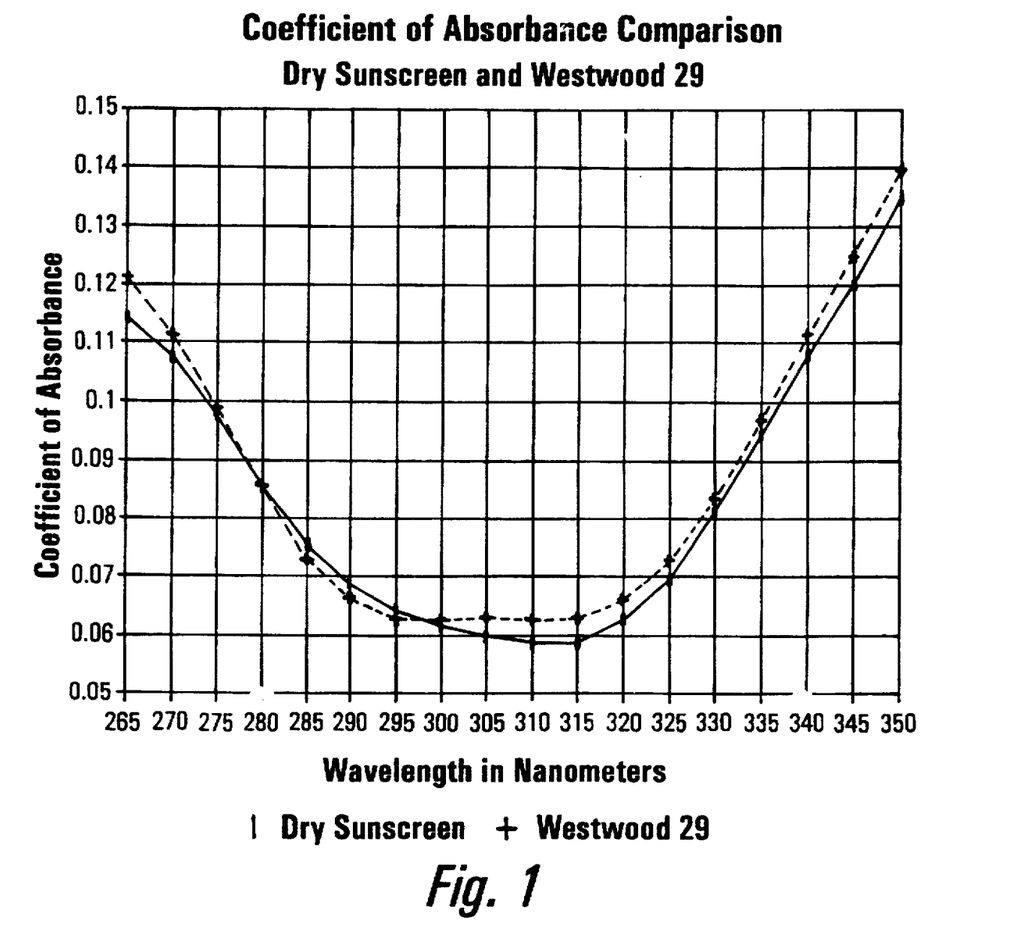

The graphic representation of the data shown in FIG. 1 and the calculated coefficient of correlation of the coefficient of absorbance (0.996) show that by this test it would be expected that the dry sunscreen will perform as an SpF 25–30 sunscreen when used at the dosage of 0.80–1.00 $mg/cm^2$.

The following other tests have been conducted which demonstrate the effectiveness of the dry screen compositions of the present invention.

EXAMPLE 3

Accelerated Stability Testing

The following test was conducted to evaluate the relative physical stability of the dry sunscreen formulation of the present invention compared to a conventional commercial sunscreen lotion under accelerated aging conditions. Accelerated aging conditions are intended to provide physical stress to the formulations in terms of temperature conditions, to accelerate the physical deterioration which would normally occur through aging.

Storage conditions: 37, 43, 25, 4 and 60 degrees centigrade (°C.) temperatures with no light, 25 degrees centigrade (°C.) with exposure to north light. Cycling from 43 degrees centigrade to −4 degrees centigrade (Freeze-thaw (F/T) cycling), with one-half week spend under each temperature condition.

Test samples: dry sunscreen formulation of the present invention and Coppertone SPF 15 Lotion.

Results: See Attached "Table #4: Dry Sunscreen Accelerated Stability Test Results" and "Table #5: Coppertone SPF 15 Lotion Accelerated Stability Test Results."

For purposes of this test, the dry sunscreen composition of the present invention included about 7.50 weight percent octyl methoxycinnamate, about 5.00 weight percent octyl salicylate, about 15.00 weight percent homosalate, about 5.00 weight percent menthyl anthranilate, about 10.00 weight percent octocrylene, about 6.00 weight percent benzohenone-3, about 0.05 weight percent propylparaben, about 0.05 weight percent BHT, about 4.49 weight percent PVP/eicosene copolymer, about 5.75 weight percent octyl-dodecyl neopentanoate, about 5.75 weight percent C12–15 alcohols benzoate, about 10.00 weight percent titanium dioxide, about 0.15 weight percent coloring agent, and about 25.26 weight percent polymethacrylate copolymer.

invention used in Example 3 during specific types of consumer usage as compared to conventional forms of commercially available sunscreen lotions.

Subjects used in testing:

The subjects selected for the testing were several professional and semi-professional golfers, a ski instructor and an avid boater. It was predetermined that all subjects typically use conventional commercially available sunscreen lotions while participating in their respective sports. Subjects tested the dry sunscreen formulation of the present invention during times of the year in which their respective sports activities are normally conducted. Subjects used dry sunscreen of the present invention during periods of intense sunlight.

Test procedure:

In these tests, each of the subjects were each given a 2-ounce sample of the dry sunscreen formulation of the present invention in a bottle with a large-pore sized sprinkler powder dispensing closure. Subjects were told that the product was a new dry form of sunscreen. Subjects were instructed to sprinkle product into their hands, to rub their hands to release the active components and to apply it to

TABLE 4

Dry Sunscreen Accelerated Stability Test Results

| Condition | 43C | 37C | 25C | 25C/W.L. | 4C | F/T | 60C |
| --- | --- | --- | --- | --- | --- | --- | --- |
| 1 Week | OK | OK | OK | OK | OK | OK | OK |
| 2 Week | OK | OK | OK | OK | OK | OK | OK |
| 3 Week | OK | OK | OK | OK | OK | OK | OK |
| 4 Week | OK | OK | OK | OK | OK | OK | OK |
| 2 Month | OK | OK | OK | OK | OK | OK | OK |
| 3 Month | OK | OK | OK | OK | OK | OK | OK |
| 4 Month | OK | OK | OK | OK | OK | OK | OK |
| 6 Month | OK | OK | OK | OK | OK | OK | Discoloring |
| 9 Month | OK | OK | OK | OK | OK | Not Done | Discoloring |
| 1 Year | Discoloring | OK | OK | OK | OK | Not Done | Discoloring |
| 15 Month | Discoloring | OK | OK | OK | OK | Not Done | Discoloring |
| 18 Month | Discoloring | OK | OK | OK | OK | Not Done | Discoloring |
| 21 Month | Discoloring | Discoloring | OK | OK | OK | Not Done | Discoloring |
| 2 Year | Discoloring | Discoloring | OK | OK | OK | Not Done | Discoloring |

TABLE 5

Coppertone SPF 15 Accelerated Stability Test Results.

| Condition | 43C | 37C | 25C | 25C/W.L. | 4C | F/T | 60C |
| --- | --- | --- | --- | --- | --- | --- | --- |
| 1 Week | OK | OK | OK | OK | OK | OK | Separated |
| 2 Week | OK | OK | OK | OK | OK | OK | Not Done |
| 3 Week | OK | OK | OK | OK | OK | OK | Not Done |
| 4 Week | OK | OK | OK | OK | OK | OK | Not Done |
| 2 Month | OK | OK | OK | OK | OK | OK | Not Done |
| 3 Month | OK | OK | OK | OK | OK | OK | Not Done |
| 4 Month | Separated | OK | OK | OK | OK | OK | Not Done |
| 6 Month | Not Done | Discolored | OK | OK | OK | OK | Not Done |
| 9 Month | Not Done | Discolored | OK | Not Done | OK | Not Done | Not Done |
| 1 Year | Not Done | Separated | OK | Not Done | OK | Not Done | Not Done |
| 15 Month | Not Done | Not Done | OK | Not Done | OK | Not Done | Not Done |
| 18 Month | Not Done | Not Done | OK | Not Done | OK | Not Done | Not Done |
| 21 Month | Not Done | Not Done | OK | Not Done | OK | Not Done | Not Done |
| 2 Year | Not Done | Not Done | OK | Not Done | OK | Not Done | Not Done |

EXAMPLE 4

Usage Testing

The following test was conducted to evaluate the performance of the dry sunscreen formulation of the present their skin surface where they would typically apply conventional lotion products during sports activities. Subjects were told that it would not be necessary to reapply the dry sunscreen composition of the present invention during the period of sports activity. Following their sports activities subjects were asked to characterize the dry sunscreen composition of the present invention's performance relative to the conventional sunscreen lotion products which they use.

The responses of the subjects were as follows:

Response of golfers: The dry sunscreen formulation of the present invention was more comfortable to wear. It did not feel greasy or heavy on skin. The dry sunscreen formulation of the present invention provided all day coverage and protection. It did not interfere with golfers grip on the handle of their clubs. During storage of the dry sunscreen composition of the present invention unit in their golf bag, the product did not leak and damage their equipment. In general, the dry sunscreen formulation of the present invention did not detract from their attention to the game, provided all day coverage and stored well.

Response of skiers: The dry sunscreen formulation of the present invention provided all day coverage and protection. It did not interfere with the contact made between the ski mask and facial skin. The dry sunscreen composition of the present invention did not soil ski clothing. The dry sunscreen formulation of the present invention was also very useable at low temperatures.

Response of boaters: The dry sunscreen formulation of the present invention provided all day protection and was comfortable to wear. It did not interfere with the grip of boaters on equipment typically used during boating. Storage of the dry sunscreen formulation of the present invention was not a problem since it did not leak.

Thus it can be seen that all of the stated objectives have been realized.

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

What is claimed is:

1. A dry sunscreen composition comprising effective amounts of:

at least one sunscreen active ingredient selected from the group consisting of octyldimethyl paba, octyl methoxycinnamate, octyl salicylate, homosalate, menthyl anthranilate, octocrylene, benzohenone-3, titanium dioxide, and zinc oxide;

a biocide selected from the group consisting of butylparaben and propylparaben;

an antioxidant selected from the group consisting of BHA, tocopherol, and BHT;

a substantivity aid selected from the group consisting of tricontanyl PVP and PVP/eicosene copolymer;

an emollient comprising octyldodecyl neopentanoate;

a solvent selected from the group consisting of: esters of propylene glycol, isopropyl alcohol, glycerine, isobutyl alcohol; octanol esters of $C_6$–$C_{18}$ fatty acids; and $C_{12-15}$ alcohols benzoate; and an entrapment polymer selected from a group of acrylates copolymers consisting of polymethacrylate copolymers wherein said copolymer has a formula with the following structure:

wherein R is an alkyl group, and x and y are repeating units.

2. The dry sunscreen composition of claim 1, wherein said alkyl is at least one member selected from a group consisting of ethyl groups and dodecyl groups and wherein a ratio of said x and y within the range of about 100:20 to about 60:20.

3. The dry sunscreen composition of claim 2, wherein said ethyl group has a formula: —$CH_2CH_2$—.

4. The dry sunscreen composition of claim 2, wherein said dodecyl group has a formula: —$(CH_2)_{11}CH_3$.

5. The dry sunscreen composition of claim 2, wherein said ratio is about 80:20.

6. The dry sunscreen composition of claim 2, wherein said polymethacrylate copolymer has a formula with the following structure:

wherein R' comprises an ethyl group and R" comprises a dodecyl group, and x and y are present in a ratio of about 80:20.

7. The dry sunscreen composition of claim 6, wherein said ethyl group has a formula: —$CH_2CH_2$—; and said dodecyl group has a formula: —$(CH_2)_{11}CH_3$.

8. The dry sunscreen composition of claim 1, wherein said effective amount of said at least one sunscreen ingredient comprise:

an amount up to about 8.0 wt % of octyldimethyl paba;

an amount up to about 7.5 wt % of octyl methoxycinnamate;

an amount up to about 5 wt % of octyl salicylate;

an amount up to about 15 wt % of homosalate;

an amount up to about 5 wt % of menthyl anthranilate;

an amount up to about 10 wt % of octocrylene;

an amount up to about 6 wt % of benzohenone-3 (oxybenzone);

an amount up to about 25 wt % of titanium dioxide; and an amount up to about 25 wt % of zinc oxide.

9. The dry sunscreen product of claim 8, wherein
said biocide selected from the group consisting of butylparaben and propylparaben is present in amounts within the range of about 0.01 wt % to about 0.2 wt %;
said antioxidant is selected from the group consisting of BHA or tocopherol and BHT is present in amounts within the range of about 0.01 wt % to about 0.2 wt %;
said substantivity aid selected from the group consisting of tricontanyl PVP and PVP/eicosene copolymer is present in amounts within the range of about 0.25 wt % to about 10.0 wt %;
said emollient is present in amounts within the range of about 0.5 wt % to about 10.0 wt %;
said solvent selected from the group consisting of C8–12 alkyl esters of: propylene glycol, isopropyl alcohol, glycerine, isobutyl alcohol; octanol esters of $C_6$–$C_{18}$ fatty acids; and C12–15 alcohols benzoate is present in amounts within the range of about 0.5 wt % to about 10.0 wt %;
said entrapment polymer selected from the group consisting of acrylates copolymer is present in amounts within the range of about 10 wt % to about 40 wt %.

10. The dry sunscreen product of claim 1, further comprising:
a coloring agent selected from the group consisting of D&C lakes, FD&C color lakes, and iron oxides.

11. The dry sunscreen composition of claim 1, wherein said effective amount of said at least one sunscreen ingredient comprises:
an amount within the range of about 2.0 wt % to 7.5 wt % of octyl methoxycinnamate;
an amount within the range of about 3.0 wt % to about 5.0 wt % of octyl salicylate;
an amount within the range of about 4.0 wt % to about 15.0 wt % of homosalate;
an amount within the range of about 3.5 wt % to about 5.0 wt % of menthyl anthranilate;
an amount within the range of about 7.0 wt % to about 10.0 wt % of octocrylene;
an amount within the range of about 2.0 wt % to about 6.0 wt % of benzohenone-3(oxybenzone); and
an amount within the range of about 2.0 wt % to about 25 wt % of titanium dioxide.

12. The dry sunscreen product of claim 11, wherein said at least one sunscreen ingredient comprises at least two members selected from the group consisting of octyldimethyl paba, octyl methoxycinnamate, octyl salicylate, homosalate, menthyl anthranilate, octocrylene, benzohenone-3, titanium dioxide, and zinc oxide.

13. The dry sunscreen product of claim 12, wherein
said biocide comprises propylparaben present in an amount within the range of about 0.01 wt % to about 0.2 wt %;
said antioxidant comprises BHT present in an amount within the range of about 0.01 wt % to about 0.2 wt %;
said substantivity aid comprises PVP and PVP/eicosene copolymer present in an amount within the range of about 0.25 wt % to about 10.0 wt %;
said emollient comprises octyldodecyl neopentanoate present in an amount within the range of about 0.5 wt % to about 10.0 wt %;
said solvent comprises $C_{12-15}$ alcohols benzoate present in an amount within the range of about 0.5 wt % to about 10.0 wt %; and said entrapment polymers comprises acrylates copolymer present in an amount within the range of about 10 wt % to about 40 wt %.

14. A dry sunscreen composition comprising:
octyl methoxycinnamate present in an amount within the range of about 2 wt % to about 7.5 wt %;
octyl salicylate present in an amount within the range of about 3 wt % to about 5 wt %;
homosalate present in an amount within the range of about 4 wt % to about 15 wt %;
menthyl anthranilate present in an amount within the range of about 3.5 wt % to about 5 wt %;
octocrylene present in an amount within the range of about 7 wt % to about 10 wt %;
benzohenone-3 (oxybenzone) present in an amount within the range of about 2 wt % to about 6 wt %;
propylparaben present in an amount within the range of about 0.01 wt % to about 2.0 wt %;
BHT present in an amount within the range of about 0.01 wt % to about 2.0 wt %;
PVP/eicosene copolymer present in an amount within the range of about 0.25 wt % to about 10.0 wt %;
octyldodecyl neopentanoate present in an amount within the range of about 0.5 wt % to about 10.0 wt %;
C12–15 alcohols benzoate present in an amount within the range of about 0.5wt % to about 10.0 wt %;
titanium dioxide present in an amount within the range of about 2 wt % to about 25 wt %; and
polymethacrylate copolymer present in an amount within the range of about 10.0 wt % to about 40.0 wt %.

15. A process for preparing dry sunscreen compositions comprising:
combining effective amounts of:
at least one sunscreen ingredient selected from the group consisting of an ingredient selected from the group consisting of octyldimethyl paba, octyl methoxycinnamate, octyl salicylate, homosalate, menthyl anthranilate, octocrylene, and benzohenone-3;
a biocide selected from the group consisting of butylparaben and propylparaben;
an antioxidant selected from the group consisting of BHA, tocopherol, and BHT; and
a substantivity aid selected from the group consisting of tricontanyl PVP, and PVP/eicosene copolymer;
to form a first section of ingredients;
heating the first section of ingredients to a sufficient temperature with substantially constant mixing until it becomes clear and homogenous;
combining effective amounts of solvents selected from the group consisting of: esters of propylene glycol, isopropyl alcohol, glycerine, and isobutyl alcohol; octanol esters of $C_6$–$C_{18}$ fatty acids; and $C_{12-15}$ alcohols benzoate; and an emollient to form a second section of ingredients by mixing at substantially ambient temperature;
adding effective amounts of at least one member selected from the group consisting of a sunscreen ingredient selected from the group consisting of zinc oxide and titanium dioxide; and coloring agents selected from the group consisting of D&C lakes, FD&C color lakes, and iron oxides, to the second section of ingredients by mixing at ambient temperature until it becomes a uniform paste;

adding the uniform paste to the first section of ingredients to form a homogenous fluid;

milling the homogenous fluid at a sufficient temperature until a predetermined size is obtained;

heating the milled homogenous fluid to a predetermined temperature;

adding a first amount of acrylates copolymer to the milled homogenous fluid and mixing to form a third section of ingredients; and adding the third section of ingredients to additional acrylates copolymer and mixing until it forms a homogenous dry sunscreen composition, wherein said acrylates copolymer has a formula with the following structure:

wherein R is an alkyl group, and x and y are repeating units.

16. The process of claim 15, wherein said alkyl group is at least one member selected from a group consisting of ethyl group and dodecyl group and x and y are present in a ratio within the range of about 100:20 to about 80:20.

17. The process of claim 16, wherein said formula is:

wherein R' is ethyl and R" is dodecyl.

18. The process of claim 15, comprising the step of holding the homogenous dry sunscreen composition in a sealed container for about twenty-four hours, whereby complete absorbance of the milled homogenous fluid onto the acrylates copolymer is achieved.

19. The process of claim 15, wherein the temperature to which the first section is heated is within the range of about 70° C. to about 85° C.

20. The process of claim 19, wherein the temperature to which the first section is heated is within the range of about 75° C. to about 80° C.

21. The process of claim 15, wherein the temperature at which the homogenous fluid is milled is within the range of about 60° C. to about 85° C.

22. The process of claim 21, wherein the temperature at which the homogenous fluid is milled is within the range of about 70° C. to about 80° C.

23. The process of claim 15, wherein the temperature to which the milled homogenous fluid is heated is within the range of about 60° C. to about 85° C.

24. The process of claim 23, wherein the temperature to which the milled homogenous fluid is heated is within the range of about 70° C. to about 85° C.

* * * * *